United States Patent [19]
Greth

[11] 3,941,786
[45] Mar. 2, 1976

[54] PROCESS FOR THE PRODUCTION OF 4-HYDROXY-6-HYDROXYMETHYLPYRIMIDINE

[75] Inventor: Erich Greth, Visp, Switzerland

[73] Assignee: Lonza Ltd., Gampe, Valais, Switzerland

[22] Filed: June 12, 1974

[21] Appl. No.: 478,733

Related U.S. Application Data

[63] Continuation-in-part of Ser. No. 258,485, June 1, 1972, abandoned.

[30] Foreign Application Priority Data

June 7, 1971  Switzerland.......................... 8251/71

[52] U.S. Cl............................................ 260/251 R
[51] Int. Cl.².................................. C07D 239/26
[58] Field of Search ................................ 260/251 R

[56] References Cited
OTHER PUBLICATIONS

Brown — "The Pyrimiones" (1962) Interscience Publishers — pp. 214–215.
Brown — "The Pyrimiones Supplement I" (1970) Interscience Publishers — p. 161.

Primary Examiner—Lewis Gotts
Assistant Examiner—D. R. Phillips
Attorney, Agent, or Firm—Christen & Sabol

[57] ABSTRACT

Process for the production of 2-R¹ substituted-4- hydroxy-5-R² substituted -6-hydroxy methyl-pyrimidines having the following general formula:

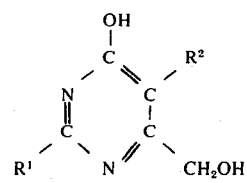

(I)

wherein R¹ can be an alkyl group, a phenyl group or —H, and wherein R² can be an alkyl group, a phenyl group or —H. The process includes reacting a 2-R¹ substituted -4-hydroxy-5-R² substituted -6-chloromethyl-pyrimidine having the following general formula:

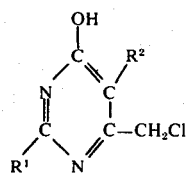

(II)

wherein R¹ and R² are defined as above, with water under reflux at a pH value of 4 to 8.

24 Claims, No Drawings

PROCESS FOR THE PRODUCTION OF 4-HYDROXY-6-HYDROXYMETHYLPYRIMIDINE

This application is a continuation-in-part of co-pending U.S. Ser. No. 258,485, filed on June 1, 1972, now abandoned.

BACKGROUND OF THIS INVENTION

1. Field of This Invention

This invention involves the production of 4-hydroxy-6-hydroxymethyl-pyrimidines, and more particularly the production of such compounds from the corresponding chloromethyl pyrimidines.

2. Prior Art 6-hydroxymethyl pyrimidines have been produced from the corresponding 6-chloromethylpyrimidines. In such cases the 6-chloromethyl compound is first converted to the 6-acetoxymethyl derivative by treatment with an aqueous silver acetate solution, and this derivative is then converted by heating with barium hydroxide in water to the 6-hydroxymethyl derivative (*Zentralblatt*, 1913, II, page 273). Such a process is cumbersome and requires a reaction of two stages. Furthermore, large quantities of silver acetate are consumed.

*Synthetic Methods of Organic Chemistry*, (W. Teilheimer, Publishers of S. Krager, Basel) 2 76 No. 237, teaches that 5-chloromethyl furfural is poured into a large quantity of boiling water so that the concentration of the developing HCl will be so weak that it will not react with the reaction product. 5-oxymethyl furfural results with a yield of 90 percent. (W. N. Haworth and W. G. M. Jones, Soc. 1944, p 667, is cited as the source.) The reaction is:

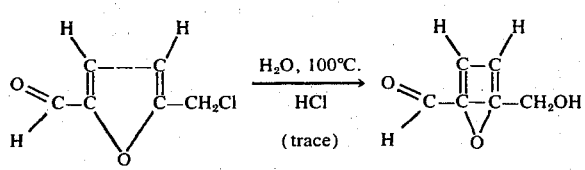

*Journal of the American Chemical Society*, 73, pp. 2,388 to 91 (1951), teaches the following reaction:

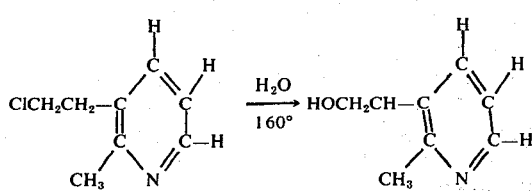

The purity was only 90 percent after two crystallization steps during its purification.

Dutch Pat. No. 126,387 teaches a process of preparing 4-chloropyrimidines (and their salts) having the following formula:

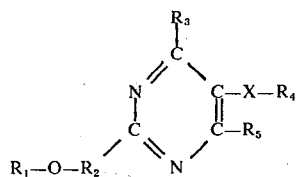

wherein: $R_1$ signifies an alkyl radical with at most 4 carbon atoms; $R_2$ an alkylene radical with at most 4 carbon atoms; $R_3$ signifies a chlorine atom; X signifies a direct bond or an alkylene radical with at most 4 carbon atoms; $R_4$ signifies a phenyl radical substituted by one or more halogen atoms, alkyl, alkoxy, or alkenyloxy groups, with each having at most 4 carbon atoms, amino, alkylamino groups with at most 4, or dialkylamino groups with altogether at most 8 carbon atoms; and $R_5$ signifies a halogen atom, an alkyl or alkoxy group with at most 4 carbon atoms, a hydroxyl group, amino group, alkylamino group with at most 4, or a dialkylamino group with altogether at most 8 carbon atoms, or an alkylene amino group interrupted possibly by oxygen with at most 7 ring atoms. The products are pharmacologically active. That Dutch patent is based on Dutch Patent Application No. 6,503,747 (Ciba) and was published prior to examination.

A typical process is:

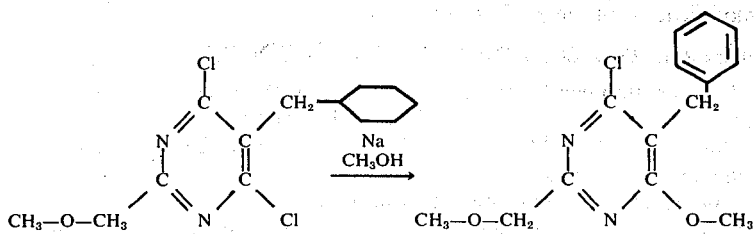

See for example, column 17, example XIV.

That Dutch patent also teaches a process for the production of pharmaceutical preparations by the mixing of a pharmacologically effective substance of a compound (obtained by the process of the Dutch patent) with a carrier.

Attention is also drawn to: U.S. Pat. No. 3,048,587; Brown, "The Pyrimidines", Interscience Publishers, (1962), pp. 214–5; Brown, "The Pyrimidines — Supplement I", Interscience Publishers, (1970), p. 161; McCasland, G. E. et al., J. Am. Chem. Soc. 68 (1946); and British Patent No. 471,416.

BROAD DESCRIPTION OF THIS INVENTION

It is the object of this invention to carry out the conversion of the 6-chloromethyl group of a corresponding pyrimidine to the 6-hydroxymethyl group in a simple manner with very high yields of a very pure product.

This invention involves a process for the production of 2-$R^1$ substituted-4-hydroxy-5-$R^2$ substituted -6- hydroxy methyl pyrimidines having the following general formula:

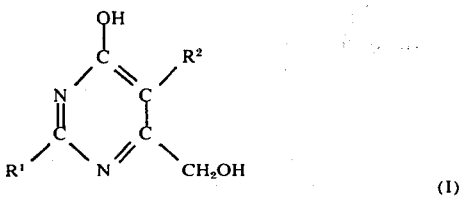

wherein $R^1$ can be an alkyl group having 1 to 10 carbon atoms, a phenyl group or —H and wherein $R^2$ can be an alkyl group having 1 to 10 carbon atoms, a phenyl group or —H. The process includes reacting a 2-$R^1$ substituted -4-hydroxy-5-$R^2$ substituted -6-chlormethyl pyrimidine having the following general formula:

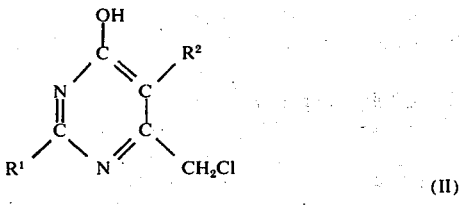

wherein $R^1$ and $R^2$ are defined as above, with water under reflux at a pH value of 4 to 8.

Preferably the pH ranges between 6 and 7. Also, preferably the pH value is maintained by the use of buffers. The pH value can be maintained by the continuous controlled addition of an alkaline reacting compounds. Alternatively, a buffer is present as the reaction starts and the reaction is periodically interrupted and an alkaline reacting compound is added thereto to maintain the pH value in the stated range. (This is a modification of the preferred embodiment.)

DETAILED DESCRIPTION OF THIS INVENTION

The reaction can be conducted at atmospheric pressures or at pressures in excess of atmospheric pressure. It has been found that pressures of up to about 20 atmospheres are effective.

The water enters into the reaction, but also serves as the solvent. The water should therefore be present in excess of that needed for the reaction; preferably 5 to 500 times more water is present, on a weight basis, than the 2-$R^1$ substituted -4-hydroxy-5-$R^2$ substituted-6-chloromethyl pyrimidine.

It is important in the process of this invention that the conversion be carried out approximately at the neutral point. Indeed, as soon as the reaction solution becomes acidic, because of a separation of HCl, secondary reactions occur which lead to an impure product having a deep brown color instead of a pure product. Naturally, there is quite a decrease in the yield. An acidic pH up to 4 can be used, but the above is why the slightly acidic or neutral pH range of 6 to 7 is preferred. The products of this invention have a purity of about 97 to 98 percent.

The pH values of 4 to 8 and preferably 6 to 7 for the reaction mixture can be maintained (i) by use of a buffer compound, for example, sodium acetate, or potassium dihydrogen phosphate-dipotassium hydrogen phosphate, or (ii) by a continuous controlled addition of an alkaline reacting compound, for example, sodium hydroxide solution. Such addition of alkali reacting compound is at the rate of consumption, in the reaction mixture, and is best coupled with an electrometric pH measurement to assure accurate control of the rate of addition.

Any compatible buffer can be used to maintain the pH value within the indicated range (or preferred range). Examples of useful buffer compounds or systems are: sodium acetate (preferred), potassium dihydrogen phosphate - dispotassium hydrogen phosphate (preferred), potassium dihydrogen phosphate - sodium hydroxide, potassium hydrogen phthalate - sodium hydroxide, potassium hydrogen phthalate, disodium hydrogen phosphate, potassium dihydrogen phosphate - disodium hydrogen phosphate, sodium dihydrogen phosphate - disodium hydrogen phosphate and MacIlvaine's Buffer Mixture (disodium acid phosphate - citric acid).

The alkaline reacting compounds can be inorganic or organic compounds. Examples of inorganic alkaline reacting compounds are sodium hydroxide, beryllium hydroxide, calcium hydroxide, and sodium carbonate. Examples of organic alkaline reacting compounds are trisobutyl amine and ethyldiisopropylamine.

Details of the definitions of $R^1$ and $R^2$ follow.

$R^1$ can be a lower alkyl group containing one to 10 carbon atoms and can be a straight chain or branch chain alkyl group. Examples of useful alkyl groups which $R^1$ can be are: methyl, ethyl, n-propyl, isopropyl, n-butyl, isobutyl, n-pentyl, isopentyl, n-hexyl, n-heptyl, n-octyl, n-nonyl, n-decyl, neopentyl, 2,4-dimethyl-3-pentyl, 2-heptyl, 3-heptyl, 2-methyl-2-heptyl, 3-methyl-2-heptyl, 4-heptyl, 2,6-dimethyl-4-heptyl, 4-ethyl-4-heptyl, 2-methyl-1-heptyl, 4-methyl-4-heptyl, 3-methyl-1-heptyl, 4-propyl-4-heptyl, 4-methyl-1-heptyl, 2,2,3,3-tetramethyl butyl, 2,3-dimethyl pentyl, 2,2,4-trimethyl pentyl, 2,4-dimethyl-3-ethyl-3-hexyl, 2-ethylhexyl, 2-butyl, t.-butyl, 2-methyl-1-butyl, 2-pentyl, 3-pentyl, 3-methyl-2-butyl, 2-methyl-2-butyl, 2-methyl-1-pentyl, 3-methyl-1-pentyl, 4-methyl-1-pentyl, 2-ethyl-1-butyl, t.-amyl, 2,3-dimethyl-1-butyl, 2-hexyl, 3-hexyl, 3-methyl-2-pentyl, 2,2-dimethyl-3-butyl, 4-methyl-2-pentyl, 2,3-dimethyl-2-butyl, 2-methyl-3-pentyl, and 3-methyl-3-pentyl, and 2-methyl- 2-pentyl.

$R^1$ can be a phenyl group.

$R^1$ can be a phenyl group or hydrogen.

$R^1$ can also be butylbenzyl, 1-butyl-2-methylbenzyl, 1,2-diethylbenzyl, 1-butyl-3-methylbenzyl, 1,3-diethylbenzyl, 1-butyl-4-methylbenzyl, 1,4-diethylbenzyl, 1-sec.-butyl-4-methylbenzyl, 1,4-di-tert.-butylbenzyl, 1-tert.-butyl-4-methylbenzyl, 1,2-diisopropylbenzyl, 1,3-diethyl-5-methylbenzyl, 1,3-diisopropylbenzyl, 1,4-diisopropylbenzyl, 1,2-dimethylbenzyl, 1,3-dimethylbenzyl, 1,4-dimethylbenzyl, 1,2-dimethyl-4-ethylbenzyl, ethylbenzyl, 1,3-dimethyl-5-ethylbenzyl, isopropylbenzyl, 1,4-dimethyl-2-ethylbenzyl, pentylbenzyl, 2,4-dimethyl-1-ethylbenzyl, propylbenzyl, 1-ethyl-4-isobutylbenzyl, 1,2,3,4-tetraethylbenzyl, 1-ethyl-3-isopropylbenzyl, 1,2,3,5-tetraethylbenzyl, 1-ethyl-4-isopropylbenzyl, 1,2,4,5-tetraethylbenzyl, 1-ethyl-2-methylbenzyl, 1-ethyl-3-methylbenzyl, 1-ethyl-4-methylbenzyl, 1-ethyl-4-propylbenzyl, 1-isopropyl-3-methylbenzyl, (4-methyl-pentyl)benzyl, 1-methyl-3-propylbenzyl, 1-methyl-4-propybenzyl, 1,2,4-triethylbenzyl, 1,2,3-trimethylbenzyl, 1-methylbenzyl and 2-methylbenzyl.

$R^2$ can be a lower alkyl group as defined for $R^1$, and the examples for $R^1$ are incorporated here for $R^2$. $R^2$ can be a phenyl group or hydrogen.

Examples of 2-R[1] substituted-4-hydroxy-5-R[2] substituted -6-chloromethyl-pyrimidines which can be used as starting materials in this invention are: 4-hydroxy-6-chloromethyl-pyrimidine, 2-isopropyl-4-hydroxy-6-chloromethyl-pyrimidine, (preferred), 2-methyl-4-hydroxy-6-chloromethyl-pyrimidine, 2-(n-decyl)-4-hydroxy-6-chloromethyl-pyrimidine, 2-(2-hexyl)-4-hydroxy-6-chloromethyl-pyrimidine, 2-phenyl-4-hydroxy-6-chloromethyl-pyrimidine, 2(2-methyl-1-pentyl)-4-hydroxy-6-chloromethyl-pyrimidine, 2-isopropyl-4-hydroxy-5-isopropyl-6-chloromethyl-pyrimidine, 2-isopropyl-4-hydroxy-5-methyl-6-chloromethyl-pyrimidine, 2-phenyl-4-hydroxy-5-methyl-6-chloromethyl-pyrimidine, 2-methyl-4-hydroxy-5-(2-hexyl)-6-chloromethyl-pyrimidine, 4-hydroxy-5-methyl-6-chloromethyl-pyrimidine, 4-hydroxy-5-(n-decyl)-6-chloromethyl-pyrimidine and 4-hydroxy-5-phenyl-6-chloromethyl pyrimidine.

The pyrimidines are known to have what is termed almost universal utility in the pharmaceutical and therapeutic fields, i.e., almost every known pyrimidine is known to have pharmaceutical or therapeutic utility. This is the opposite of the steroid field. U.S. Pat. No. 3,048,587 at col. 1, lines 18 to 20, states that compounds having a pyrimidine nucleus are widely applicable in the pharmaceutical field. The following are various homologs, etc., of the pyrimidines of this invention which clearly establish that the pyrimidines of this invention have the utility of, or would clearly be expected by one ordinarily skilled in the art to have the utility of, the various analogs, homologs, etc., of the pyrimidines of this invention. This clearly establishes utility for the pyrimidines of this invention.

McCasland et al., Jour. Am. Chem. Soc., Vol. 68, 1946, pp. 2390–95, discloses the hydrochloride of the compound:

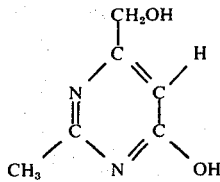

and teaches one ordinarily skilled in the art to expect that such compounds are antimalarials.

U.S. Pat. No. 3,299,067 teaches compounds having the formula:

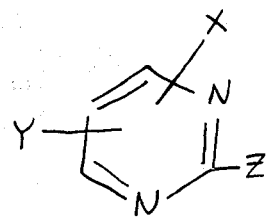

wherein Z is chlorine or bromine, wherein X and Y each are lower alkoxy, hydroxy, or hydroxylower-alkyl. Such compounds are useful in preparing certain 2-[1'-(benzyl and phenyl)-4'-piperazinyl]-pyrimidine derivatives, which are useful as peripherical vasodilators, analgesics and anti-inflammatory agents.

U.S. Pat. No. 3,631,045 teaches compounds having the formula:

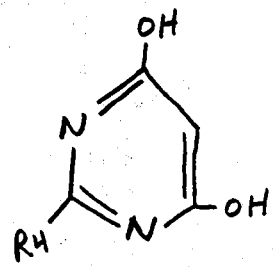

wherein $R_4$ can be lower alkyl, phenyl or lower alkylphenyl. Such compounds are useful in preparing 4,5-diamino-7H-pyrrolo [2,3-d] pyrimidine derivatives which have central nervous system activity as depressants.

U.S. Pat. No. 3,651,063 teaches a compound having the formula:

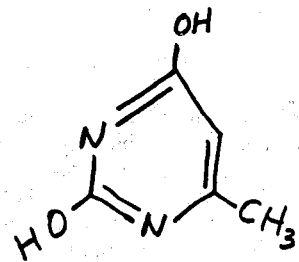

Such a compound is useful in producing 5-aminomethyl-2,4-dihydroxy-6-methyl pyrimidine derivatives, which potentiate the efficiency of antibiotics such as chloramphenicol and josamycin against the likes of Staphylococcus aureus.

U.S. Pat. No. 3,290,306 teaches compounds having the formula:

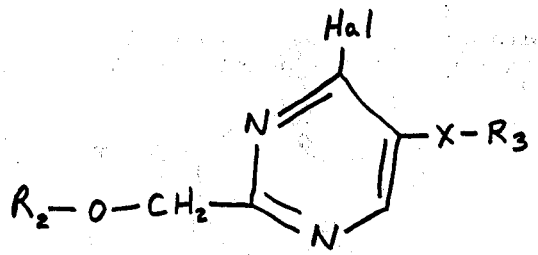

wherein Hal is a halogen, e.g., chlorine, wherein Y is hydroxy, wherein $R_2$ is lower alkyl, wherein X is lower alkylene or a direct bond and wherein $R_3$ is phenyl. Such compounds are useful as sedatives, hypnotics and narcotics. That patent also teaches 2-(R-O-Alk)-4-hydroxy-5-($R_1$-X)-6-Z-pyrimidines wherein Z is hydrogen, lower alkyl or hydroxy, wherein Alk is lower alkylene, wherein X is lower alkylene or a direct bond, wherein R is a lower hydrocarbon radical or aliphatic character and wherein $R_1$ is an aromatic radical. Such compounds are useful in preparing the first group of compounds.

U.S. Pat. No. 3,758,472 teaches compounds having the formula:

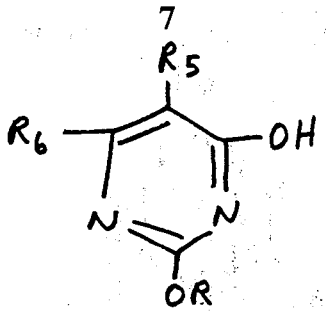

wherein $R_1$ and $R_5$ and $R_6$ are the same or different alkyl having 1 to 8 carbon atoms. Such compounds are useful as fungicides. Such compounds are also useful in making compounds having the formula:

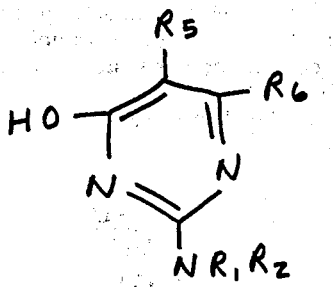

wherein $R_1$ is hydrogen or an alkyl group having 1 to 4 carbon atoms and $R_2$ is an alkyl group having 1 to 4 carbon atoms. Such compounds, where $R_1$ and $R_2$ are hydrogen, are the same as compounds taught in U.S. Pat. No. 3,676,443, which are intermediate in preparing certain fungicides and pesticides.

U.S. Pat. No. 3,382,248 discloses compounds having the formula:

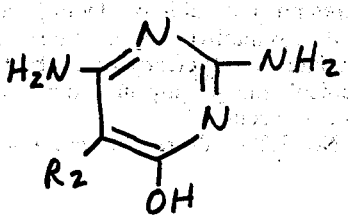

wherein $R_2$ or lower alkoxyalkyl, which are useful in producing compounds having the formula:

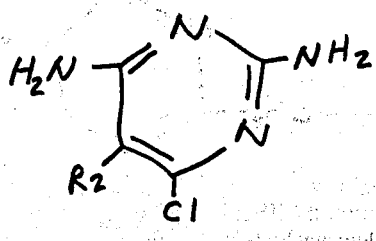

wherein $R_2$ is hydrogen or lower alkoxyalkyl, which in turn are useful in producing certain 1,2-dihydro-1-hydroxypyrimidines. The latter compounds are useful as antihypertensive agents.

U.S. Pat. No. 3,328,169 teaches pyrimidines substituted with groups such as hydroxy, amino or alkyl (examples are 2,4-diamino-6-hydroxy-pyrimidine and 2-hydroxy-4,6-diamino-pyrimidine). Such compounds are useful in producing certain menadione bisulfite adducts of organic nitrogenous bases, which are antihemorrhagic agents and have strong Vitamin K activity.

U.S. Pat. No. 3,126,271 teaches compounds having the formula:

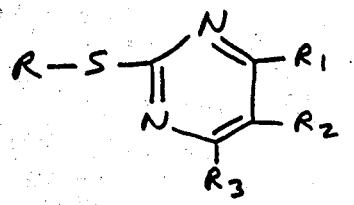

wherein R can be phenyl or phenyl alkyl, $R_1$ can be methoxy, $R_2$ can be hydrogen or methyl, and $R_3$ can be methoxy. Such compounds are useful as herbicides, particularily against crab grass, foxtail, wild oats, lamb's-quarters, red-root pigweed and Jimpson weed or field bondweed.

U.S. Pat. No. 3,317,536 discloses compounds having the formula:

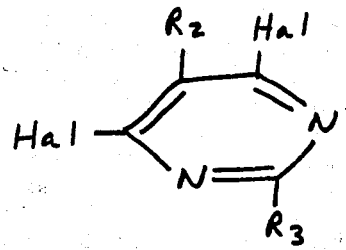

wherein Hal is a halogen atom, wherein $R_2$ is lower alkyl, lower alkoxy, alkoxyalkyl, hydroxyalkyl or hydroxy-alkoxy and wherein $R_3$ is hydrogen, lower alkyl or hydroxy-alkoxy. Such compounds are useful in producing certain 4-benzenesulfonamido-pyrimidine derivatives, which are useful as blood sugar depressants. That patent also teaches compounds having the formula:

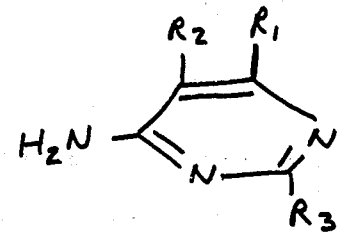

wherein $R_2$ and $R_3$ are as above for the first compounds and wherein $R_1$ is hydrogen, alkoxy-alkoxy or hydroxy-alkoxy. Such compounds are useful in producing the above 4-benzenesulfonamido-pyrimidine derivatives.

U.S. Pat. No. 3,499,898 disclose compounds having the formula:

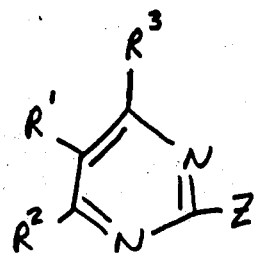

wherein R¹ is amino, wherein R² is hydrogen or hydroxy, wherein R³ is hydrogen or hydroxy and wherein Z is amino or hydroxy. Such compounds are useful in preparing certain substituted amino or hydroxy. Such compounds are useful in preparing certain substituted amino pyrimidines, which have anti-inflammatory and anti-pyretic properties.

U.S. Pat. No. 3,455,921 teaches compounds having the formula:

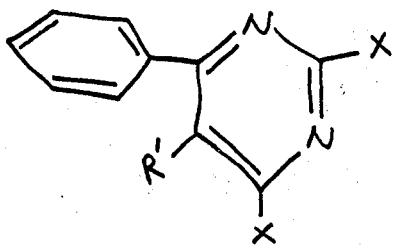

wherein X is hydroxy or chlorine and wherein R¹ is alkoxyalkyl in which the alkoxy and alkyl each contain less than 8 carbon atoms. Such compounds are useful as anti-hypercholesterolemics, anti-inflammatories and anti-germicidal when in the dihydroxy orm and as antimicrobials when in the dichloro form. Such compounds are useful in producing certain 2,4-diazido-6- phenylpyrimidines, which are useful as antiinflammatories and are analgesic and hypotensive.

U.S. Pat. No. 3,707,560 teaches compounds having the formula:

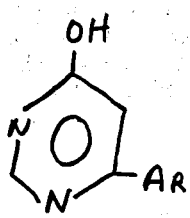

where Ar can be phenyl. Such compounds are useful in making 4-amino-6-arylpyrimidines and salts thereof, which are useful as inhibitors of platelet aggregation and bronchodilators in mammals.

U.S. Pat. No. 3,741,968 teaches that the salts having the formula:

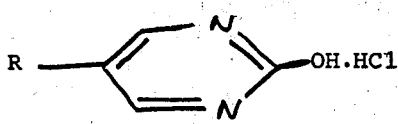

wherein R is hydrogen, F, Cl, Br or I, are used to prepare certain 0-(2-pyrimidyl) phosphates, which are useful as insecticides. More specifically, such phosphates are useful as insecticides against the corn root worm, house fly, Mexican bean beetle, pea aphid, plum curculio, southern army worm, two-spotted mite and mosquito.

The following examples describe aspects of this invention, but are not meant to limit the scope of this invention. In the examples and throughout the rest of this application, percentages, parts and ratios are on a weight basis unless otherwise stated or otherwise obvious to one ordinarily skilled in the art.

EXAMPLE 1

9.33 gm of 2-isopropyl-4-hydroxy-6-chloromethyl-pyrimidine (0.0495 mole) and 13.60 gm of sodium acetate (having 3 molecules water of crystallization, 0.10 mole) were heated in 200 ml of water under reflux (atmospheric pressure). At the 5, 24 and 48 hours periods in the reaction, the reaction was interrupted and the pH of the reaction mixture was adjusted to 7 with 1N sodium hydroxide solution. After 72 hours overall duration, the reaction was discontinued. (Throughout this reaction period the pH was always between 5 and 8.) 50 ml of 1N hydrochloric acid were added. Over a 5 hour period, acetic acid and water were distilled off, with the lost water continuously being replaced. The distillation residue was brought to a pH of 5 and was evaporated until dry. The dry residue subsequently was extracted with methylene chloride in a Soxhlet extractor (separation of NaCl and sodium acetate). After distillation off of the methylene chloride, the 2-isopropyl-4-hydroxy-6-hydroxymethyl-pyrimidine was obtained. The yield of the product was 93.72 percent and the product has a purity of 97.9 percent. The melting point of the product was 186.2° to 186.5°C.

An analysis of the product was

|  | C | H | N | O |
|---|---|---|---|---|
| Found: | 57.5% | 7.0% | 16.7% | 18.8% |
| Calculated | 57.08% | 7.19% | 16.66% | 19.02% |

EXAMPLE 2

Example 1 was repeated except that no buffer (sodium acetate) and no sodium hydroxide were used. When the 2-isopropyl-4-hydroxy-6-chloromethyl-pyrimidine was treated with water under reflux, the pH value of the reaction solution in the course of the reaction to about 1. The resultant product had a deep brown color, indicating it was very impure, and the yield of this impure product amounted to 80 percent. This example represents an embodiment outside of this invention.

EXAMPLE 3

Example 1 was repeated except that the sodium acetate was replaced with an equal molar amount of a buffer mixture of potassium dihydrogen phosphate and dipotassium hydrogen phosphate. The resultant product was very pure and obtained in a very high yield.

EXAMPLE 4

Example 1 was repeated except that the reaction was conducted at a reflux pressure of five atmospheres. At the 0.5, 1 and 2 hour periods, the reaction was interrupted and the pH of the reaction mixture was adjusted to 7 with 1N sodium hydroxide solution. After 3 hours overall duration, the reaction was stopped. The resultant product was very pure and obtained in a very high yield.

EXAMPLE 5

Example 1 was repeated except that the sodium acetate was replaced with an equal molar amount of a buffer mixture of disodium acid phosphate and citric acid. The resultant product was very pure and obtained in a very high yield.

EXAMPLE 6

Example 1 was repeated except that the sodium acetate was replaced with an equal molar amount of a buffer mixture of potassium hydrogen phthalate and sodium hydroxide. The resultant product was very pure and obtained in a very high yield.

EXAMPLE 7

Example 1 was repeated except that 0.40 moles of sodium acetate were used and that the reaction was not interrupted after 5, 24 and 48 hours for the addition of sodium hydroxide. The resultant product was very pure and obtained in a very high yield.

EXAMPLE 8

Example 1 was repeated except that the sodium hydroxide was replaced with potassium hydroxide. The resultant product was very pure and obtained in a very high yield.

EXAMPLE 9

Example 1 was repeated except that the sodium hydroxide was replaced with sodium carbonate. The resultant product was very pure and obtained in a very high yield.

EXAMPLE 10

Example 1 was repeated except that the 2-isopropyl-4-hydroxy-6-chloromethyl pyrimidine was replaced with an equal molar amount of 4-hydroxy-6-chloromethyl-pyrimidine. The resultant product was very pure and obtained in a very high yield.

EXAMPLE 11

Example 1 was repeated except that the 2-isopropyl-4-hydroxy-6-chloromethyl pyrimidine was replaced with an equal molar amount of 4-hydroxy-5-methyl-6-chloromethyl-pyrimidine. The resultant product was very pure and obtained in a very high yield.

EXAMPLE 12

Example 1 was repeated except that the 2-isopropyl-4-hydroxy-6-chloromethyl-pyrimidine was replaced with an equal molar amount of 2-isopropyl-4-hydroxy-5-butylbenzyl-6-chloromethyl-pyrimidine. The resultant product was very pure and obtained in a very high yield.

EXAMPLE 13

9.33 gm of 2-isopropyl-4-hydroxy-6-chloromethyl-pyrimidine was placed in 200 ml. of water. Enough sodium hydroxide was added to the mixture to adjust the pH to 7. The mixture was under reflux (atmospheric pressure) for 72 hours. Whenever the pH shifted from a pH of 7, as measured by a pH electrometer, enough sodium hydroxide was automatically added to the solution and the product was treated as in Example 1. The resultant product was very pure and obtained in a very high yield.

EXAMPLE 14

When Example 1 was repeated using no buffer, but only using aqueous sodium hydroxide or potassium carbon, an impure product was obtained. The yield was very low, only about 80 percent. It is believed that the byproduct is an oligomere having the formula:

[structure of oligomer]

What I claim is:

1. A process for the production of 2-$R^1$ substituted-4-hydroxy -5-$R^2$ substituted-6-hydroxymethyl-pyrimidines having the following formula:

[structure of pyrimidine product with $R^1$, $R^2$, OH, and $CH_2OH$ substituents]

wherein $R^1$ can be an alkyl group having 1 to 10 carbons, phenyl group or —H, and wherein $R^2$ can be an alkyl having 1 to 10 carbons, a phenyl group or —H, which comprises reacting a 2-$R^1$ substituted-4-hydroxy-5-$R^2$ substituted-6-chloromethyl-pyrimidine having the following formula:

[structure of pyrimidine starting material with $R^1$, $R^2$, OH, and $CH_2Cl$ substituents]

wherein $R^1$ and $R^2$ are defined above, with water under reflux at a pH value of 4 to 8, said pH not being outside the stated range during said reaction.

2. A process as described in claim 1 wherein $R^1$ is hydrogen.

3. A process as described in claim 1 wherein $R^1$ is an alkyl having 1 to 10 carbons.

4. A process as described in claim 1 wherein $R^1$ is a phenyl group.

5. A process as described in claim 1 wherein $R^1$ is isopropyl and $R^2$ is hydrogen.

6. A process as described in claim 1 wherein $R^2$ is hydrogen.

7. A process as described in claim 1 wherein $R^2$ is an alkyl having 1 to 10 carbons.

8. A process as described in claim 1 wherein $R^2$ is a phenyl group.

9. A process as described in claim 1 wherein $R^1$ is isopropyl.

10. A process as described in claim 1 wherein $R^1$ is hydrogen and $R^2$ is hydrogen.

11. A process as described in claim 1 wherein $R^1$ is hydrogen and $R^2$ is an alkyl having 1 to 10 carbons.

12. A process as described in claim 1 wherein $R^1$ is an alkyl having 1 to 10 carbons and $R^2$ is an alkyl having 1 to 10 carbons.

13. A process as described in claim 1 wherein $R^1$ is an alkyl having 1 to 10 carbons and $R^2$ is hydrogen.

14. A process as described in claim 1 wherein the pH value ranges between 6 and 7.

15. A process as described in claim 1 wherein the pH value is maintained by the use of a buffer.

16. A process as described in claim 1 wherein said buffer is sodium acetate or a mixture of potassium dihydrogen phosphate and dipotassium hydrogen phosphate.

17. A process as described in claim 1 wherein the pH value is maintained by the continuous controlled addition of an alkaline reacting compound.

18. A process as described in claim 1 wherein said alkaline reacting compound is sodium hydroxide.

19. A process as described in claim 1 wherein the reaction is conducted at atmospheric pressure or at a pressure in excess of atmospheric pressure.

20. A process as described in claim 1 wherein said 2-$R^1$ substituted-4-hydroxy-5-$R^2$ substituted-6-chloromethyl pyrimidine is 2-isopropyl-4-hydroxy-6-chloromethyl-pyrimidine or 4-chloromethyl-6-hydroxy-pyrimidine.

21. A process as described in claim 1 wherein the reaction is conducted for between 1 and 100 hours.

22. A process as described in claim 1 wherein a buffer is present as the reaction starts and wherein the reaction is periodically interrupted and an alkaline reacting compound is added thereto to maintain the pH value in the stated range.

23. A process as described in claim 22 wherein said buffer is sodium acetate and said alkaline reacting compound is sodium hydroxide.

24. A process as described in claim 1 wherein $R_1$ is methyl and $R_2$ is hydrogen.

* * * * *